United States Patent [19]

Prete

[11] Patent Number: 5,584,125
[45] Date of Patent: Dec. 17, 1996

[54] RESPIRATOR MASK SIZING GUIDE

[75] Inventor: Christopher L. Prete, Cranberry Township, Pa.

[73] Assignee: Mine Safety Appliances Company, Pittsburgh, Pa.

[21] Appl. No.: 470,545

[22] Filed: Jun. 6, 1995

[51] Int. Cl.⁶ .................................................. G01B 3/38
[52] U.S. Cl. ..................... 33/501.45; 33/512; 128/774
[58] Field of Search ..................... 33/512, 513, 501.45; 128/774, 777

[56] References Cited

U.S. PATENT DOCUMENTS

| | | | |
|---|---|---|---|
| 1,161,504 | 11/1915 | Miller | 33/512 |
| 1,976,045 | 10/1934 | Sorenson | 33/513 |
| 2,107,543 | 2/1938 | Miller | 409/35 |
| 2,154,158 | 4/1939 | Gustavson | 235/54 R |
| 2,780,004 | 2/1957 | Rosenbaum | 33/512 |
| 3,377,712 | 4/1968 | Farkas et al. | 33/512 |
| 4,718,850 | 1/1988 | Knebelman | 433/72 |
| 4,729,260 | 3/1988 | Dudden | 475/125 |
| 4,843,720 | 7/1989 | Kim | 33/513 |

*Primary Examiner*—William A. Cuchlinski, Jr.
*Assistant Examiner*—Vagnola Khamvongsa
*Attorney, Agent, or Firm*—James G. Uber; H. E. Bartony, Jr.

[57] ABSTRACT

The present invention provides a sizing guide for assisting in the initial determination of an appropriate size of respirator mask for a user thereof. The sizing guide has at least a first sizing gap having a known width such that comparison of the width of the first sizing gap with the length between a pair of facial landmarks such as the sellion landmark and the menton landmark provides an initial determination of the appropriate size respirator mask for the user which can then be fit tested. Preferably, the sizing guide also has a second sizing gap having a known width different from the width of the first sizing gap.

9 Claims, 5 Drawing Sheets

RESPIRATOR MASK SIZING GUIDE

FIELD OF THE INVENTION

The present invention relates to a sizing guide for facial dimensions, and particularly to a sizing guide for fitting a respiratory face mask to the face of a user of the respiratory face mask.

BACKGROUND OF THE INVENTION

Numerous devices have been developed over the years to measure the location of various facial points as well as to measure the dimensions of various facial features. Most such devices have been developed to assist medical professionals in, for example, forming dentures or restructuring facial bones. See e.g., U.S. Pat. No. 1,976,045; U.S. Pat. No. 2,107,534; U.S. Pat. No. 4,843,720, U.S. Pat. No. 4,279,260; U.S. Pat. No. 3,377,712, U.S. Pat. No. 2,154,158 and U.S. Pat. No. 4,718,850.

There has been little success, however, in developing a practical facial measurement device for assisting in the fitting of facially worn apparatuses such as respirator masks. In general, facial measurement devices developed for use in the medical and dental arts are either inoperative or too complicated, cumbersome and/or expensive for use in sizing respirator masks. Nonetheless, it is extremely important to fit a respirator face mask properly to the face of the person wearing the mask to ensure an adequate seal of the mask to that person's face because such respirator masks are usually worn for protection in environments containing extremely hazardous gases where a breach in the mask seal may result in serious injury or death.

Currently, users of respirator face masks must be fitted for such respirator masks by a trial-and-error process wherein the user must sequentially try on one or more actual respirator masks and be fit tested in each such mask until an appropriate size is identified. See OSHA Respiratory Protection Standard, 29 C.F.R. 1910.134. This procedure can become very inconvenient and time consuming, especially in an industrial setting where a large number of individuals must be fitted. ANSI Z88.2-1992 entitled "Standard Practices for Respiratory Protection" sets forth the proper procedures for conducting a fit test program.

It is, therefore, very desirable to develop a practical device and/or method for assisting in the selection of a correct respirator face mask for a user to avoid repeated fit tests.

SUMMARY OF THE INVENTION

Generally, the present invention provides a sizing guide for assisting in properly selecting the appropriate size of mask For a user of a respirator mask. The sizing guide comprises at least a first sizing gap having a known width. Comparison of the width of the first sizing gap with the length between a first landmark on the face of the user and a second landmark upon the face of the user provides an approximation of the appropriate size respirator mask for the user. A number of pairs of landmarks located upon the human face provide very good reference points. Such landmark pairs include, but are not limited to, the following: (1) the sellion landmark and the menton landmark; (2) the left zygion landmark and the right zygion landmark on the zygomatic arches (or upper cheekbones) and (3) the left cheilion landmark and the right cheilion landmark (at the corners of the mouth). The distance between the landmarks of any such single pair of facial landmarks can be used, or the distance between the landmarks of more than one pair of landmarks may be used in determining an initial size. Such measurements are particularly useful in fitting "half-mask" respirators such as the Comfo® TopFit respirator face mask available from Mine Safety Appliances Company.

The sizing guide preferably further comprises a second sizing gap having a width different from the width of the first sizing gap to provide further information as of the appropriate size respirator mask.

The present invention also provides generally a sizing guide for assisting in the determination of an appropriate size respirator mask for a user, comprising: n–1 sizing gaps, wherein n is the number of respirator mask sizes available. Each of the n–1 sizing gaps has a different width, such that comparison of the width of at least one of the n–1 sizing gap with the length between a first landmark and a second landmark on the face of the user (as described above) provides an approximation of the appropriate size of respirator mask for the user.

The present invention thus provides a simple device and method for quickly and inexpensively selecting the appropriate respirator mask for a user that marks a significant improvement over the current trial-and-error method of fitting such masks. Other details and advantages of the present invention will become apparent as the following description of the invention proceeds.

BRIEF DESCRIPTION OF THE DRAWINGS

In the accompanying drawings, preferred embodiments of the invention and preferred methods of practicing the invention are illustrated in which.

DETAILED DESCRIPTION OF THE INVENTION

Figure 1A:
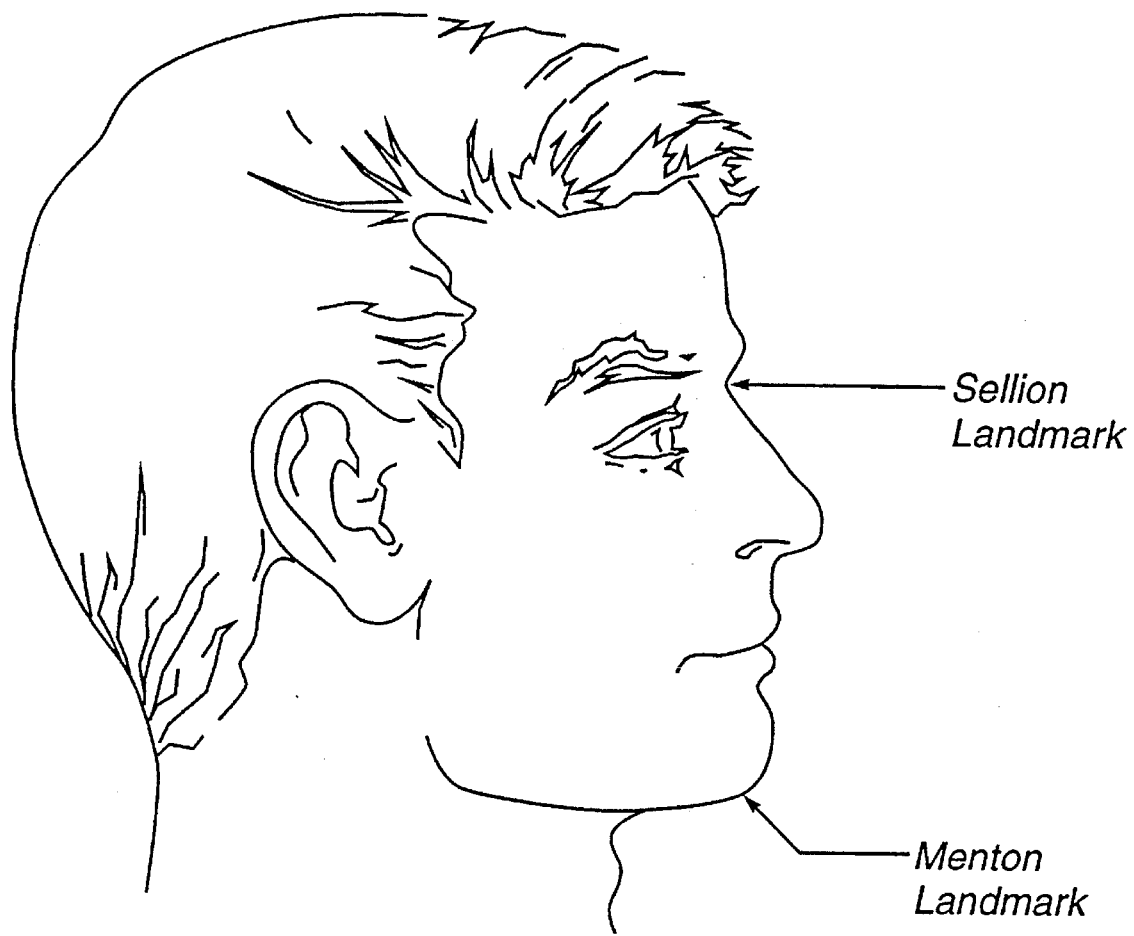
FIG. 1A illustrates the location of the sellion landmark and the menton landmark on the human face.
Figure 1B:
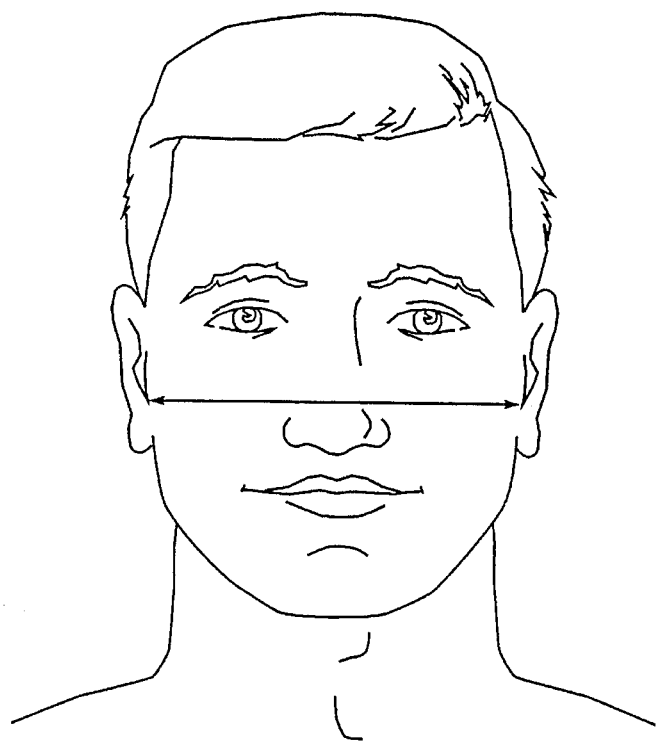
FIG. 1B illustrates the location of the-left zygion landmark and the right zygion landmark on the human face.
Figure 1C:
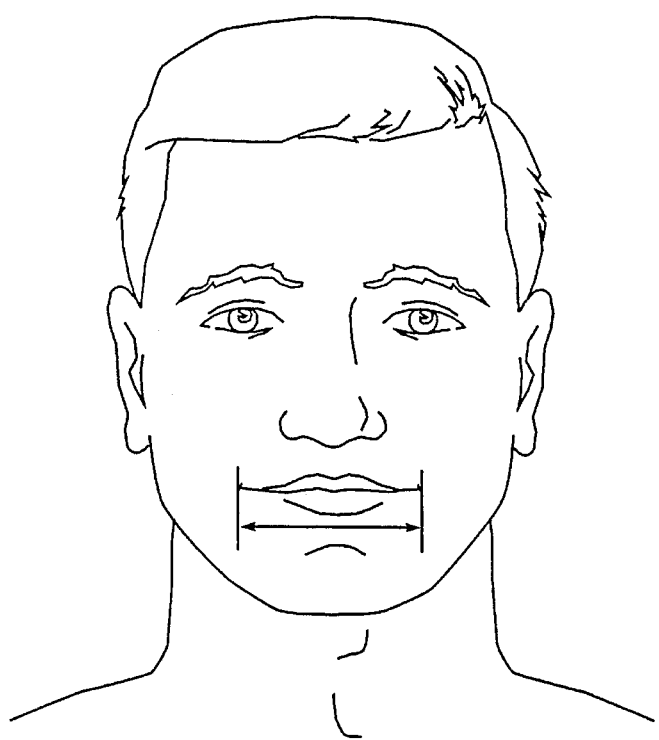
FIG. 1C illustrates the location of the left cheilion landmark and the right cheilion landmark on the human face.

Applicant has discovered that the distances between pairs of landmarks on the human face provide valuable information in the initial fitting of respirator face masks to an individual user. For example, the distance between the deepest depression of the bridge of the nose, that is, the sellion landmark, and the lowest point of the jawbone under the chin, that is, the menton landmark, (see FIG. 1A) provides an excellent measurement for the initial fitting of a respirator mask to an individual user. Other suitable pairs of facial landmarks include the left zygion landmark and the right zygion landmark (see FIG. 1B) and the left cheilion landmark and the right cheilion landmark (see FIG. 1C). The present invention provides a sizing guide 10 that uses these pairs of facial points of reference or landmarks to initially select the appropriate size of respirator mask for a user.

Preferably, the distance between the sellion landmark and the menton landmark is used.

Figure 2:
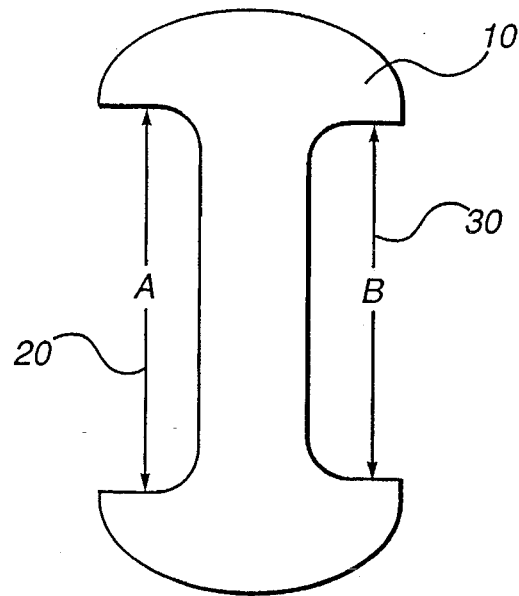
FIG. 2 illustrates an embodiment of a sizing guide comprising two sizing gaps.

Sizing guide 10 is best illustrated in FIG. 2. Preferably, sizing guide 10 comprises a piece of substantially rigid material, such as a cardboard or plastic, having at least a first sizing gap 20. More preferably, sizing guide 10 also comprises a second sizing gap 30. First sizing gap 20 has a known width A which is greater than known width B of second sizing gap 30. In one embodiment of sizing guide 10 for use in connection with the Comfo TopFit respirator of Mine Safety Appliances Company, for example, width A equals approximately 4.764 in., while width B equals approximately 4.173 in.

Figure 3:
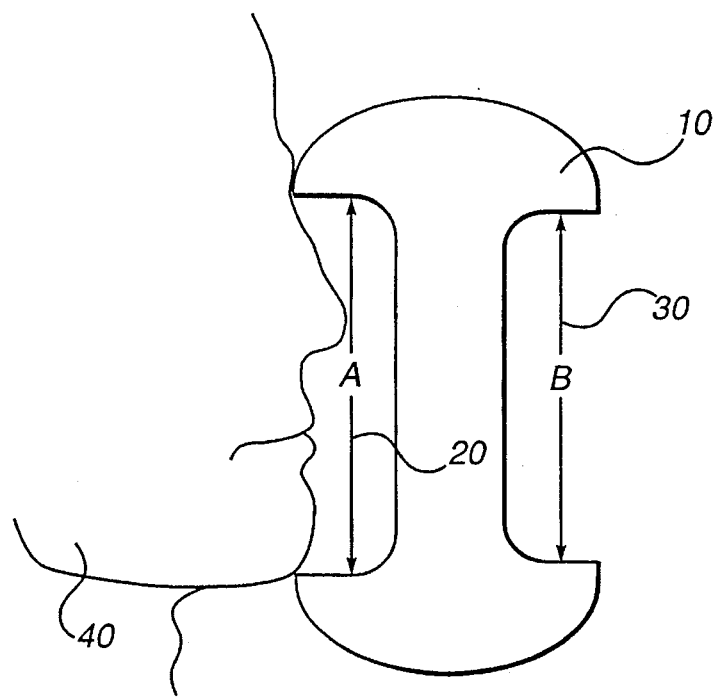
FIG. 3 illustrates the use of an embodiment of a sizing guide to determine an appropriate respirator face mask size.

In using sizing guide 10, the user 40 preferably stands, looking straight ahead with his or her mouth closed and teeth together. As illustrated in FIG. 3, user 40 first places first sizing gap 20 to his or her face to determine if the length L between the sellion and menton landmarks is greater than or less than width A of sizing gap 20. Width A of sizing gap 20 is preferably such that if length L is greater than width A, it is likely that user 40 requires a first certain size respirator mask (for example, a "large" size respirator mask).

If length L is less than width A, user 40 then preferably compares width B of sizing gap 30 with length L. If length L is greater than width B, user 40 likely requires a second certain size respirator mask (for example, a "medium" size respirator mask). If length L is less than width B, user 40 likely requires a third certain size respirator mask (for example, a "small" size respirator mask).

Figure 4:
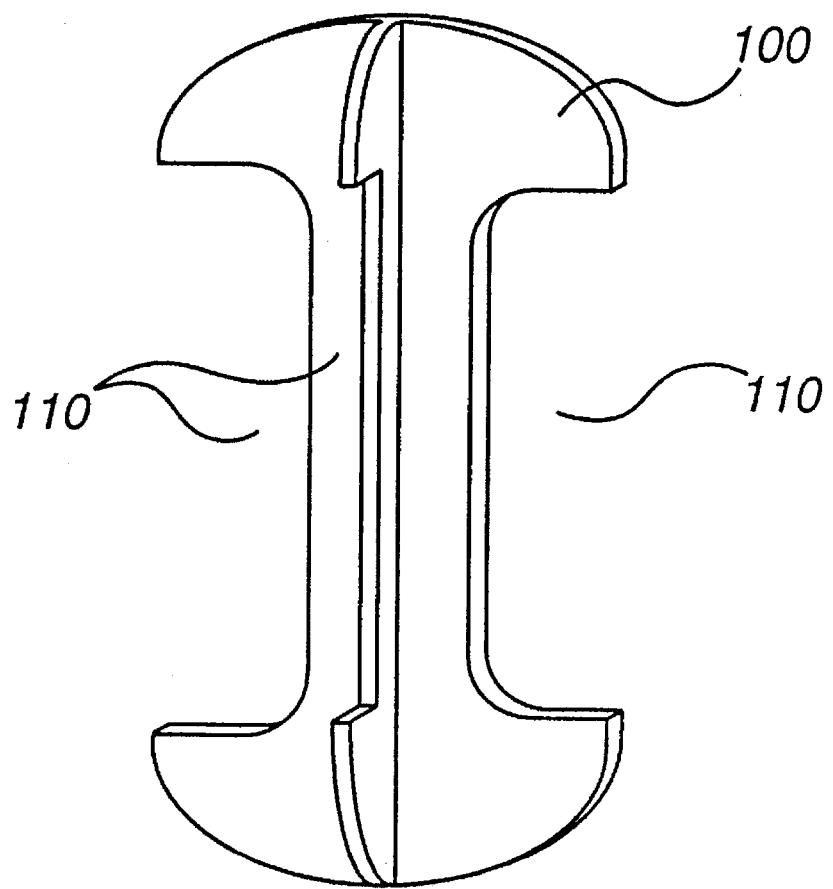
FIG. 4 illustrates an embodiment of a sizing guide comprising three sizing gaps.

As clear to one of ordinary skill in the art, the present sizing guide preferably comprises n−1 sizing gaps wherein n is the number of sizes of respirator masks available. For example, if only two (2) sizes of respirator masks are available, sizing guide 10 may comprise a single sizing gap. If four (4) sizes of respirator masks are available, a sizing guide 100 (see FIG. 4) comprising three (3) appropriately dimensioned sizing gaps 110 is preferably provided.

Figure 5:
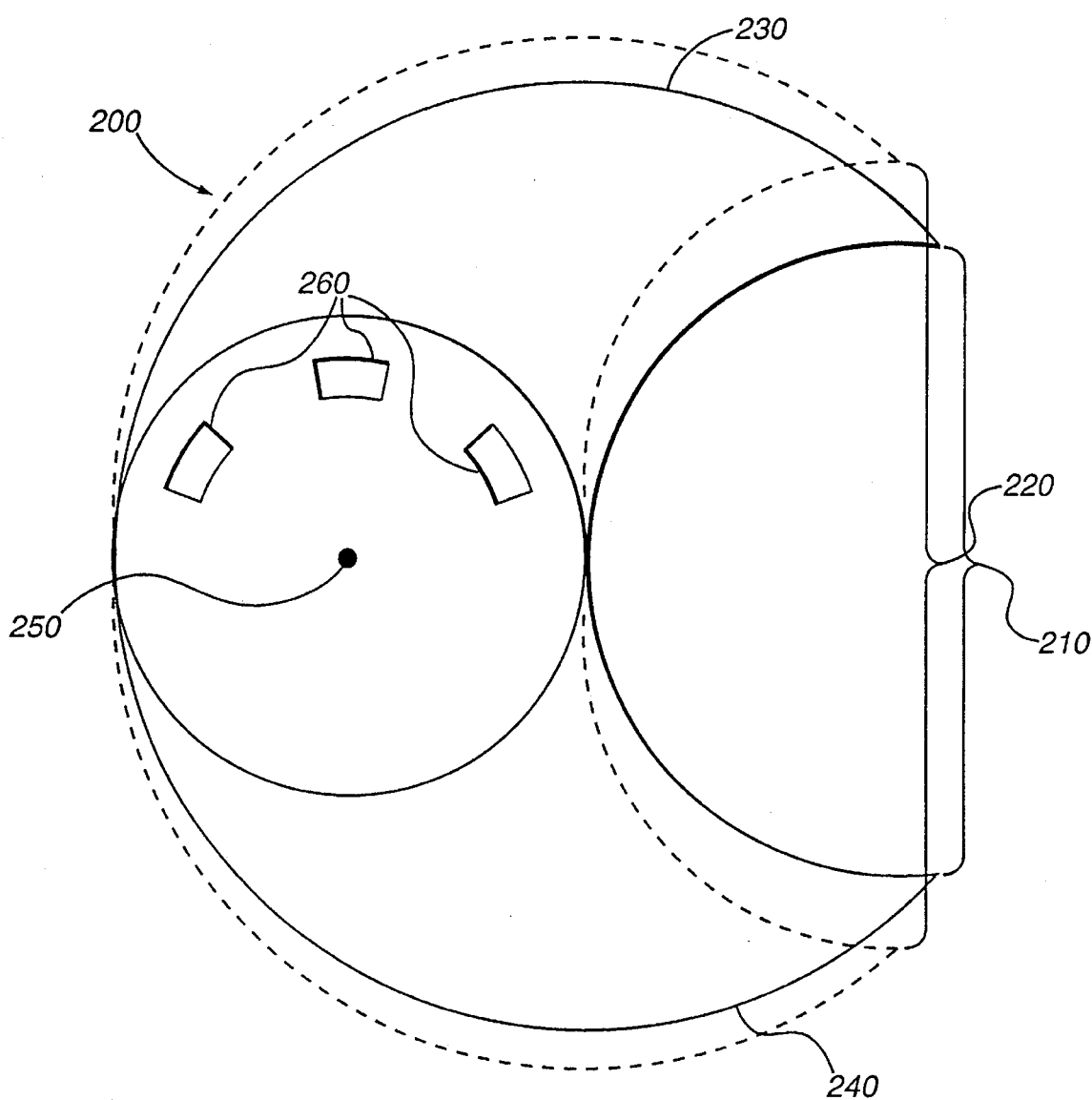
FIG. 5 illustrates an embodiment of a sizing guide comprising an adjustable sizing gap.

As illustrated in FIG. 5, a sizing guide 200 may be provided which is adjustable between two or more sizing gaps of predetermined widths 210 and 220. For example, sizing gap 200 comprises two rotatable members 230 and 240, rotatable around a common axis 250. Preferably, indicator markings 260 are provided to indicate the appropriate relative positions of members 230 and 240 to achieve a desired sizing gap width. Moreover, stop or abutment means (not shown) are preferably provided to assist in maintaining a desired sizing gap width after adjustment thereto.

Although the present invention has been described in detail in connection with the above embodiments, it is to be understood that such detail is solely for that purpose and that variations can be made by those skilled in the art without departing from the spirit of the invention except as it may be limited by the following claims.

What is claimed is:

1. A sizing guide for assisting in the determination of an appropriate size respirator mask for a user thereof, comprising: a first sizing gap and a second sizing gap, the first sizing gap having a first known width and the second sizing gap having a known width different from the first known width of the first sizing gap, such that comparison of the first sizing gap and the second sizing gap with the length between a first landmark and a second landmark on the face of the user provides an approximation of the appropriate size respirator mask for the user.

2. The sizing guide of claim 1 wherein the first landmark is the sellion landmark and the second landmark is the menton landmark.

3. The sizing guide of claim 1 wherein the first landmark is the left zygion landmark and the second landmark is the right zygion landmark.

4. The sizing guide of claim 1 wherein the first landmark is the left cheilion landmark and the second landmark is the right cheilion landmark.

5. A sizing guide for assisting in the determination of an appropriate size respirator mask for a user thereof, comprising: n−1 sizing gaps, wherein n is the number of respirator mask sizes available, each of the n−1 sizing gaps having a different width, such that comparison of the width of at least one of the n−1 sizing gap with the length between a first landmark and a second landmark on the face of the user provides an approximation of the appropriate size respirator mask for the user and wherein the first and second landmarks, respectively, are from the group consisting of: the sellion and menton landmarks, the left zygion and right zygion landmarks, and the left cheilion and right cheilion landmarks.

6. A method for selecting an appropriate size of respirator face mask for a user thereof, comprising: comparing the length between a first landmark and a second landmark on the face of the user with a sizing gap having a known width.

7. The method of claim 6 wherein the first landmark is the sellion landmark and the second landmark is the menton landmark.

8. The method of claim 6 wherein the first landmark is the left zygion landmark and the second landmark is the right zygion landmark.

9. The method of claim 6 wherein the first landmark is the left cheilion landmark and the second landmark is the right cheilion landmark.

* * * * *